(12) United States Patent
Fein et al.

(10) Patent No.: US 6,591,123 B2
(45) Date of Patent: Jul. 8, 2003

(54) OXIMETER SENSOR WITH DIGITAL MEMORY RECORDING SENSOR DATA

(75) Inventors: Michael E. Fein, deceased, late of Mountain View, CA (US), Marcia Fein, Legal representative; Paul D. Mannheimer, Danville, CA (US); Adnan Merchant, Fremont, CA (US); Charles Porges, Orinda, CA (US); David Swedlow, Danville, CA (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 09/943,805

(22) Filed: Aug. 30, 2001

(65) Prior Publication Data

US 2002/0038081 A1 Mar. 28, 2002

Related U.S. Application Data

(60) Provisional application No. 60/229,616, filed on Aug. 31, 2000.

(51) Int. Cl.[7] .................................................. A61B 5/00
(52) U.S. Cl. ....................................... 600/323; 600/331
(58) Field of Search ................................. 600/309–310, 600/322–326, 331

(56) References Cited

U.S. PATENT DOCUMENTS

| | | |
|---|---|---|
| 3,720,199 A | 3/1973 | Rishton et al. |
| 3,790,910 A | 2/1974 | McCormack |
| 4,303,984 A | 12/1981 | Houvig |
| 4,446,715 A | 5/1984 | Bailey |
| 4,621,643 A | 11/1986 | New, Jr. et al. |
| 4,684,245 A | 8/1987 | Goldring |
| 4,700,708 A | 10/1987 | New, Jr. et al. |
| 4,734,873 A | 3/1988 | Malloy et al. |
| 4,845,649 A | 7/1989 | Eckardt et al. |
| 4,858,615 A | 8/1989 | Meinema |
| 4,862,872 A | 9/1989 | Yabe et al. |
| 4,942,877 A | 7/1990 | Sakai et al. |
| 5,008,843 A | 4/1991 | Poelsler et al. |
| 5,016,198 A | 5/1991 | Schreiber |
| 5,058,588 A | 10/1991 | Kaestle |
| 5,070,732 A | 12/1991 | Duncan et al. |
| 5,162,725 A | 11/1992 | Hodson et al. |
| 5,246,003 A | 9/1993 | DeLonzor |
| 5,259,381 A | 11/1993 | Cheung et al. |
| 5,347,476 A | 9/1994 | McBean, Sr. |
| 5,365,462 A | 11/1994 | McBean, Sr. |
| 5,371,128 A | 12/1994 | Ulman et al. |

(List continued on next page.)

FOREIGN PATENT DOCUMENTS

| | | |
|---|---|---|
| WO | WO 93/06776 | 4/1993 |
| WO | WO97/29678 | 8/1997 |

*Primary Examiner*—Eric F. Winakur
*Assistant Examiner*—Matthew Kremer
(74) *Attorney, Agent, or Firm*—Townsend and Townsend and Crew LLP; Steven J. Cahill

(57) ABSTRACT

The present invention provides a memory chip for use in an oximeter sensor, or an associated adapter or connector circuit. The memory chip allows the storing of different data to provide enhanced capabilities for the oximeter sensor. In addition to providing unique data to store in such a memory, the invention describes unique uses of data stored in such a memory. The data stored in the memory chip may include information relating to use of the oximeter sensor. For example, the memory chip may encode a sensor model identification that can be displayed on a display screen when the sensor is connected to an oximeter monitor. The memory may also encode a range of operating parameters such as light levels over which the sensor can function or a maximum drive current. The operating parameters are read and interpreted by a controller circuit to control the pulse oximetry system.

11 Claims, 1 Drawing Sheet

U.S. PATENT DOCUMENTS

| | | |
|---|---|---|
| 5,429,129 A | 7/1995 | Lovejoy et al. |
| 5,443,801 A | 8/1995 | Langford |
| 5,528,519 A | 6/1996 | Ohkura et al. |
| 5,645,059 A | 7/1997 | Fein et al. |
| 5,660,163 A | 8/1997 | Schulman et al. |
| 5,720,293 A | 2/1998 | Quinn et al. |
| 5,800,350 A | 9/1998 | Coppleson et al. |
| 5,830,121 A | 11/1998 | Enomoto et al. |
| 5,855,609 A * | 1/1999 | Knapp .......................... 623/11 |
| 5,987,343 A | 11/1999 | Kinast |
| 6,044,283 A | 3/2000 | Fein et al. |
| 6,104,938 A * | 8/2000 | Huiku et al. ................. 600/322 |
| 6,308,089 B1 * | 10/2001 | von der Ruhr .............. 600/338 |
| 6,360,114 B1 * | 3/2002 | Diab et al. ................... 600/336 |
| 6,377,829 B1 * | 4/2002 | Al-Ali ......................... 600/323 |

* cited by examiner

OXIMETER SENSOR WITH DIGITAL MEMORY RECORDING SENSOR DATA

CROSS-REFERENCES TO RELATED APPLICATIONS

This application claims priority to U.S. Provisional Patent Application No. 60/229,616, filed Aug. 31, 2000, which is hereby incorporated by reference herein.

BACKGROUND OF THE INVENTION

The present invention relates to oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

An encoding mechanism is shown in U.S. Pat. No. 4,700,708, the disclosure of which is incorporated herein by reference. This mechanism relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary, a coding resistor is placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe.

U.S. Pat. No. 5,259,381 recognizes that the coded value of the wavelength of the red LED provided by a coding resistor may be inaccurate, since the actual wavelength can vary with temperature. Accordingly, this patent teaches including a temperature sensor in the oximeter probe to measure the actual temperature. With the actual temperature, and the coded wavelength value, a look-up table can be consulted to determine the actual LED wavelength for that temperature.

Another method of storing coded information regarding the characteristics of the LEDs is shown in U.S. Pat. No. 4,942,877 assigned to Minolta. This patent discloses using an EPROM memory to store digital information, which can be provided in parallel or serially from the sensor probe to the remote oximeter. The memory is described as storing coefficients for the saturation equation, wavelength, sub-wavelength (where 2 peaks for LED), half-width of wavelength spectrum emitted by LED, intensity of LEDS or ratio, and on time of LEDS (written by the processor).

Other examples of coding probe characteristics exist in other areas. Multiple calibration values are sometimes required, with this making the circuitry more complex or requiring many leads. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another probe with digital characterization information stored in a PROM, which is read serially using a shift register.

Typically, the coding element is mounted in the probe itself. For instance, U.S. Pat. No. 4,621,643 shows the coding resistor mounted in the probe element itself. In addition, U.S. Pat. No. 5,246,003 shows the coding resistor being formed with a printed conductive material on the probe itself.

In some devices, an electrical connector coupled by a cable to a device attached to a patient may include a coding element. For example, U.S. Pat. No. 3,720,199 shows an intra-aortic balloon catheter with a connector between the catheter and a console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

U.S. Pat. No. 5,645,059 teaches using a modulated signal to provide the coded data to a remote analyzer. U.S. Pat. No. 5,429,129 shows using a voltage regulator to produce a specific voltage value in response to an attempt to read by the analyzer.

Hewlett-Packard Company U.S. Pat. No. 5,058,588 teaches an oximeter sensor with an encoding element that could be resistor, ROM, or customized integrated circuit. The encoding element encodes the type of sensor (in particular, type indicating area of placement on body—finger, ear, foot, arm; also, the type of sensor can indicate transmission/reflection type, or adult/neonate {indicating correction to be performed on theoretical oxygen saturation, allow switching between physiological limits such as minimum/maximum pulse rates for adults/neonates}; the maximum driving current may be adapted according to type of sensor, and contact of sensor with tissue can be tested by means of an attenuation measurement if sensor type is known).

Nellcor U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

A number of catheter patents also discuss encoding information in the catheter. Sentron U.S. Pat. No. 4,858,615 teaches encoding the type of sensor, type number, serial number, date of production, safe use life of the sensor, correction data for non-linearity, pressure sensitivity, offset, and temperature sensitivity.

Interflo Medical Published PCT Application No. PCT/US92/08263, Publication No. WO 93/06776 teaches encoding patient specific data, size, manufacture date, batch number, sterilization date, expiration date, transducer number and type, manufacturer's name and address, thermistor heating element resistance, filament efficiency, program segments or patient historical data., format version for the calibration data, trademark information, catheter unique serial number, ship date, other date and time information, security code to identify manufacturer, thermal mass, filament composition, coefficient of resistance, layout byte, checksum, copyright, number of seconds since a certain date, patient weight, patient height, timestamp of 1st CO data point, and a count of all CO data points in EEPROM.

Dulex-Ohmeda of Boulder, Colo. markets an oximeter sensor product that encodes data into resistor values representing pointers to a lookup table containing coefficients (as in U.S. Pat. No. 4,700,708) as well as indicating a range of LED drive current to use with the sensor. The LEDs are driven with a higher or lower drive currents depending upon the value of the resistor in a particular sensor.

Honeywell U.S. Pat. No. 4,303,984 (expires Dec. 14, 1999) describes a memory which stores characterization information, such as linearization information for a pressure sensor. Alnor Instrument U.S. Pat. No. 5,162,725 describes storing both calibration and ID information in a sensor memory. Seimans U.S. Pat. No. 5,016,198 describes a coding memory in a sensor with data for defining sensor's characteristic curve. McBean U.S. Pat. No. 5,365,462 describes a date code in a sensor memory. Honeywell U.S. Pat. No. 4,734,873 describes a pressure sensor with a PROM storing coefficients for a polynomial. Robert Bosch U.S. Pat. No. 4,845,649 describes a PROM in a sensor storing correcting data.

McBean U.S. Pat. No. 5,371,128 relates to EEPROM in sensor with sensor type code and calibration data. McBean U.S. Pat. No. 5,347,476 describes an accuracy code. Otax U.S. Pat. No. 5,528,519 shows a PROM in a connector for oximeter.

Square D Company U.S. Pat. No. 5,070,732 shows calibration data in a sensor memory. Baxter U.S. Pat. No. 5,720,293 talks about different calibration information for a catheter, including a security code (encryption is discussed), serial number, model number, ID data such as calibration, manufacture, sterilization and ship date or other date and time information, a software program segment, security code for identifying whether sensor made by same manufacturer as monitor manufacturer, filament or transducer resistance, heat transfer coefficient, thermal mass, filament composition and coefficient of resistance, layout byte, copyright notice, checksum, random data bytes. Porsche U.S. Pat. No. 5,008,843 describes a sensor with EEPROM ID and characteristics data.

BRIEF SUMMARY OF THE INVENTION

The present invention provides a memory chip for use in an oximeter sensor, or an associated adapter or connector circuit. The memory chip allows the storing of different data to provide enhanced capabilities for the oximeter sensor. In addition to providing unique data to store in such a memory, the invention describes unique uses of data stored in such a memory. The data stored in the memory chip includes information relating to use of the oximeter sensor. For example, the memory chip may encode a sensor model identification that can be displayed on a display screen when the sensor is connected to an oximeter monitor. The memory may also encode a range of operating parameters such as light levels over which the sensor can function or a maximum drive current. The operating parameters are read by a controller circuit which uses the data read from the memory chip to control the functioning of the pulse oximetry system.

DETAILED DESCRIPTION OF THE INVENTION

Figure 1:
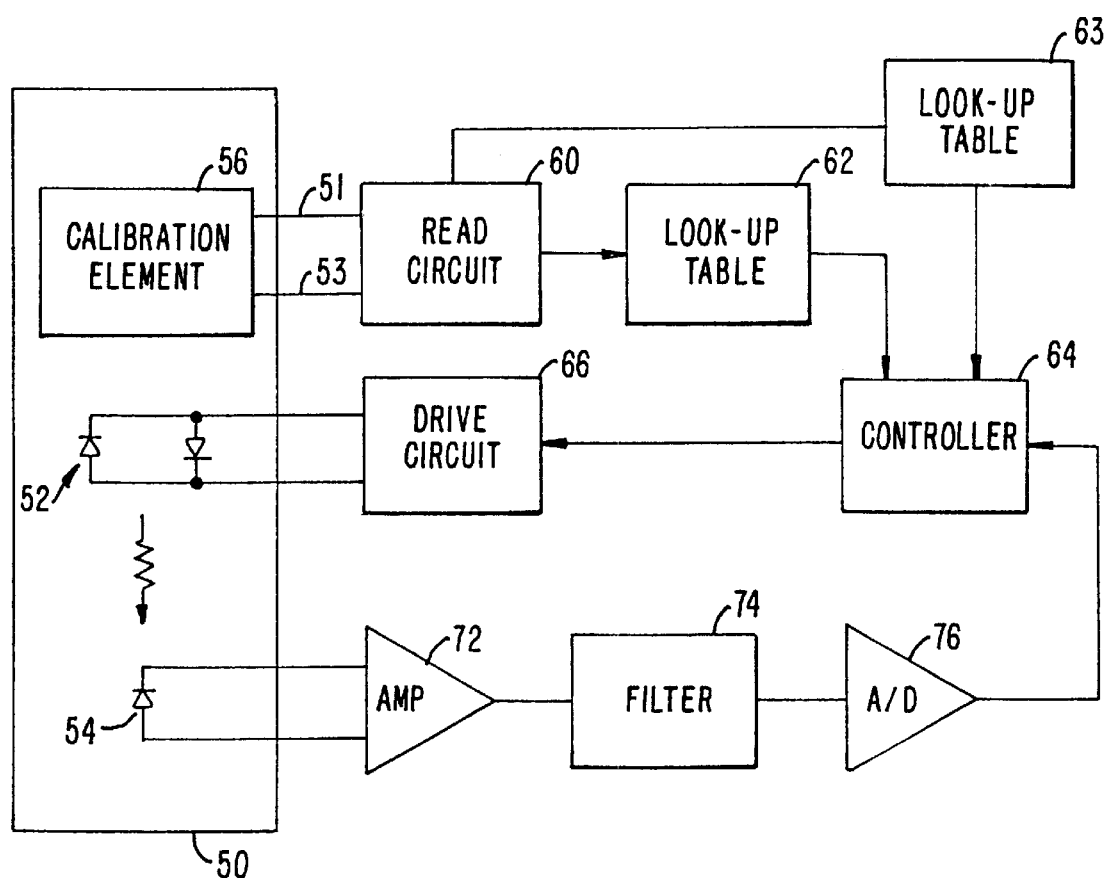
FIG. 1 is a block diagram of a pulse oximeter system in accordance with the present invention.

FIG. 1 is a block diagram of a pulse oximeter system incorporating a calibration memory element 56 according to the invention. In one embodiment, memory element 56 is a two-lead semiconductor digital memory chip. The calibration element is part of the sensor 50 which also includes red and infrared LEDs 52 as in the prior art, along with a detector 54. If desired, LEDs 52 may be replaced with other light emitting elements such as lasers.

The oximeter includes read circuit 60, drive circuit 66, look-up tables 62 and 63, controller 64, amplifier 72, filter 74, and analog-to-digital converter 76. Read circuit 60 is provided for reading multiple coded values across the two leads 51, 53 connected to calibration element 56. One value is provided to a look-up table 62 to determine appropriate wavelength dependent coefficients for the oxygen saturation calculation, as in the prior art. The other value(s) are then provided to another look up table(s) 63 which provides input (e.g., coefficients) to other calculations performed by controller 64. These additional calculations may enhance the performance and/or safety of the system. Controller 64 provides signals to a drive circuit 66, to control the amount of drive current provided to LEDs 52.

As in the prior art, detector 54 is connected through an amplifier 72 and a filter 74 to an A/D converter 76. This forms a feedback path used by controller 64 to adjust the drive current to optimize the intensity range of the signal received. For proper operation the signal must be within the analog range of the circuits employed. The signal should also be well within the range of A/D converter 76 (e.g., one rule that may be applied is to adjust LED drives and amplifier gains so that both red and IR signals fall between 40% and 80% of full scale reading of converter 76). This requires correct and independent settings for both the red and infrared LEDs. The current invention allows for another feedback path which may alter the LED settings based on other sensor characteristics contained in the coding of the calibration element 56, which is discussed in further detail below.

Memory 56 may, for example, be implemented as a random access memory (RAM), a FLASH memory, a programmable read only memory (PROM), an electrically erasable PROM, a similar programmable and/or erasable memory, any kind of erasable memory, a write once memory, or other memory technologies capable of write operations. Various types of data useful to a pulse oximetry system can be stored in memory 56. For example, data indicating a sensor model identification code corresponding to a particular sensor model can be encoded in memory 56. Also, an action can be encoded into memory element 56 indicating an action to be performing by the oximeter monitor in response to reading the sensor model identification code.

For example, an identification code in the form of text indicating the specific model of sensor can be digitally encoded into memory 56 and read by the oximeter monitor when the sensor is connected to the oximeter. An action indicating that the sensor model text is to be displayed by the oximeter monitor on a display screen can also be encoded in memory 56. The identification code can be displayed in human readable form on a display screen connected to the pulse oximeter monitor. The identification code allows the oximeter instrument to display a text string indicating what sensor model is being used, e.g. "Nellcor OXISENSOR II D-25," "Adult Digit Sensor," or "Agilent N-25."

Alternately, display text for a plurality of specific models of pulse oximeter sensors can be stored in a lookup table coupled in parallel with lookup tables 62 and 63 in the pulse oximeter monitor. The pulse oximeter monitor reads a sensor code from memory 56 when the sensor 50 is connected to the oximeter. The sensor identification code stored in memory 56 is used to locate display text stored in a lookup table that corresponds to a specific sensor model. The oximeter can display the display text for the specific sensor model on a display screen for viewing.

The present invention eliminates the need for printing a model name and number on the sensor itself. Even when model names and numbers are printed on a sensor, the text may become illegible after several uses. Displaying text that corresponds to a specific sensor model can be highly useful for users of pulse oximetry sensors. For example, it may be important to identify a sensor model so that instructions relating to a particular sensor model in the manufacturer's handbook can be identified. In addition, it may be necessary to identify a sensor model name or identify number when corresponding with the manufacturer.

Digitally encoded data indicating a sensor model type in memory 56 or in a lookup table may be used to determine whether a sensor model is compatible with a particular pulse oximeter monitor. For example, memory 56 may contain a code indicating a sensor model type that is read by controller 64. Memory 56 can also encode an action indicating that controller 64 is to compare the code from memory 56 with a list of codes in a lookup table (or other oximeter monitor memory device) to determine if the sensor is compatible. If controller 64 successfully matches the code read from the sensor, the display text indicating the sensor model type is displayed on the display screen. If controller 64 does not recognize the code, an error message may be displayed on the display screen indicating that the oximeter monitor does not recognize the sensor, and the oximeter may refuse to operate until the sensor is replaced.

A code can be stored in the sensor memory 56 identifying the sensor manufacturer. An action indicating a use for the code by the oximeter can also be stored in memory 56. The code is read by controller 64 and is used for the purpose indicated by the action. The action may, for example, indicate that the code in memory 56 is to be used to indicate operability with oximeter monitors of other manufacturers. Controller 64 can recognize certain codes as indicating compatible oximeter sensors. If the oximeter monitor does not recognize the code, then controller 64 can display an error message on a display screen indicating that the sensor is not compatible, and/or controller 64 can shut down circuitry in the oximeter monitor that senses signals from the sensor until the sensor is replaced with a compatible sensor.

Other information may also be encoded into memory 56, read by the oximeter monitor and displayed for user reference. For example, language codes or country codes can be stored in memory 56, read, and displayed to the user. The user can select a language or country code so that messages are displayed such as error messages are displayed in the selected language or a language corresponding to the selected country. Messages may also be encoded into memory 56. For example, safety messages relating to the proper use of the sensor can be encoded in memory 56 and displayed on a display screen in human-readable form.

It is often desirable to upgrade the algorithms that are used by the oximeter to determine blood oxygen saturation levels, pulse rates, pulse amplitude, blood pressure, and other patient data as technology progresses and the operating parameters (such as filter coefficients) are refined. Because oximeter sensors are typically much less expensive to replace than oximeter monitor instruments, it is desirable to encode data corresponding to the updated algorithms in the sensors rather than in the oximeter monitors.

One method for performing these updates is by encoding revisions to the algorithms used for calculating the patient parameters in memory within the oximeter monitor, while encoding updated software code or tuning coefficients in sensor memory 56. The updated code or coefficients correspond to updated algorithms that are read by the oximeter monitor so that the updated algorithms can be applied to the standard algorithms preprogrammed into the oximeter. For example, a line of software code in an algorithm used by the oximeter monitor can be replaced by a updated line of code stored in memory 56.

Controller 64 can read the updated code or coefficients from memory 56 and apply the updated algorithms to signals received from detector 54 to determine accurate blood oxygen saturation levels, pulse rates, pulse amplitudes, perfusion data, blood pressure, and other patient data. The updated algorithms can also be used to allow only supported features to be used. In the preferred embodiment, once updated, the new code or coefficients become permanently stored in the oximeter monitor, along with a new algorithm revision number, and are utilized for all future sensor use until later updated.

Encoding a sensor model identification code could also be used to accommodate sensor-specific operating parameters such as LED drive currents or "sensor off" characteristics (as an alternative to programming the value of drive current or "off" characteristics themselves). Under normal operating conditions, photosignals coming from the sensor LEDs generally fall within a certain range. When a sensor is removed from a patient, or falls off on it's own, the photosignal usually changes. This is particularly true for the reusable clip-style sensor, because in their normal disconnected state, the LEDs shine directly onto the photodetector unimpeded by, for example, tissue! By programming a "threshold photocurrent" into memory chip 56, reliable detection of a "sensor is off the patient" condition can be accomplished. In this example, exceeding a certain detected threshold light level is a sure sign the sensor isn't on a finger or other opposed site.

For certain other sensors, a low light level may be indicative of the sensor being off. An adhesive sensor, for example, lays flat when in it's natural state—little LED light may reach the detector. Encoding an expected range of light levels for the specific model of sensor being used into memory 56 allows enhanced detection of when the sensor is improperly placed or has been removed. When controller 64 senses that the light level output detector by photodetector 54 has fallen below or exceeded the expected range of light levels encoded into memory 56, the oximeter monitor can display an "sensor off" message on a display screen indicating to the medical personnel that the sensor is not in an operable position and that valid data cannot be detected (i.e., a sensor off condition). The oximeter monitor can also emit an alarm signal until the light level detected by photodetector 54 reaches the expected range.

If desired, expected ranges of light levels (or other parameters such as pulse size) that are specific to a particular patient may be encoded and saved into memory 56 by the clinical through the oximeter. The oximeter compares the expected range for the parameters encoded into memory 56 with data received from the photodetector to determine a sensor off condition each time the sensor is used until the range data is overwritten with new data. This is advantageous because light levels, pulse sizes, and other parameters detected by the photodetector can vary significantly from patient to patient.

Existing pulse oximeter sensors determine whether a sensor is off the patient, or not in good contact, by using a number of metrics. Those metrics include pulse size, pulse variability, IR/Red correlation, light level variability, pulse shape, and pulse regularity. Not only the light level, but any of these other values could vary depending on the type of sensor, the characteristics of an individual patient, and the location on the body where the sensor is to be applied. Thus, sensor memory 56 could encode information about the expected variation in any of these metrics for the particular sensor type or model or a particular patient, for use in determining if a sensor is off from any combination of these or other metrics as an indication that the sensor is off the patient.

For example, pulses could be typically weaker on the forehead compared to the finger. Memory device 56 of an oximeter sensor designed for use on the forehead of a patient can be encoded with a range of pulse sizes as well as a range of light levels that are expected from that particular oximeter sensor model. If desired, memory 56 can encode a range of numbers based upon light level and pulse size (and other parameters). For example, memory 56 can encode a range of numbers representing the expected range of pulse size times light level received from detector 54 for a specific sensor model.

Controller 64 reads and decodes the pulse size, light level range, and other data encoded in memory 56. Controller 64 then compares the expected pulse size and light level range data with the information received from detector 54. When the pulse size and/or light level data received from detector 54 exceeds or falls below the expected range data encoded in memory 56, the oximeter monitor displays an output message, e.g., a warning of a poor signal, on the display screen indicating that the sensor is not operable or emits an alarm signal. Further details of a Method and Circuit for Indicating Quality and Accuracy of Physiological Measurements are discussed in U.S. patent application Ser. No. 09/545,170, filed Apr. 6, 2000 to Porges, et al., which is incorporated by reference herein in its entirety.

Running LEDs 52 at a high drive current results in more light output from the LEDs, thus improving the signal-to-noise ratio of the blood oxygen saturation signal from detector 54, but comes at a cost of causing additional heat dissipation (i.e., the LEDs run "hotter"). As current flows through the sensor LEDs, the LED emits heat (i.e., the LED power=LED drive current times the voltage drop across the LED). The majority of the energy output by the LEDs is dissipated as heat, and the smaller portion of the energy output by the LEDs is emitted as light. This heat typically causes the temperature of the skin under the sensor to rise by an amount that that depends on the heat dissipation properties of the sensor. Current safety regulations and guidelines limit the temperature of the skin contacting portions of the sensor to remain at or below 41° C. Sensors that do a poor job of directing the heat away from the skin contacting surface, should use a lower LED drive current. Sensors with good thermal management can utilize higher drive currents without risk to the patient.

Accordingly, by encoding the maximum safe LED drive current into the sensor itself, the oximeter instrument can utilize the highest safe drive current for the sensor being used to attain the greatest amount of LED light without risk of injury. The maximum safe drive current allowed to achieve a skin temperature at or below a maximum level can be determined in advance through testing for a given oximeter sensor model. That maximum drive current can be encoded into memory 56 and read by controller 64 when the sensor is connected to the oximeter monitor. Controller 64 then communicates with drive circuit 66 to drive LEDs 52 at or near the maximum drive current value read from memory 56, but to prevent circuit 66 from driving LEDs 52 with a current that exceeds the maximum drive current.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiments disclosed, but that the invention will include all embodiments and equivalents falling within the scope of the claims.

What is claimed is:

1. An oximeter monitor system comprising:
   a sensor that includes a light emitter, a light detector, and a memory device, wherein the memory device stores an ID code tat identifies a sensor model of the sensor, and the memory device stores an action indicating that text is to be displayed in response to reading the ID code; and
   a monitor that reads the ID code and the action from said memory device, decodes said ID code, and displays the text on a display screen as indicated by the action, wherein the text indicates the sensor model.

2. The oximeter monitor system of claim 1 wherein the memory device stores a maximum safe drive current for the light emitter in said sensor.

3. The oximeter monitor system of claim 1 wherein the memory device stores an expected range for signals received from the light detector in said sensor.

4. The oximeter monitor system of claim 3 wherein signals from said light detector being outside the expected range indicate a sensor-off condition.

5. An oximeter system comprising:
   an oximeter sensor that includes a light emitting element, a light detecting element, and a memory device for storing digital data, said digital data comprising an identification code that identifies a sensor model of said oximeter sensor and an action to be performed by an oximeter monitor coupled to the oximeter sensor in response to reading the identification code; and
   an oximeter monitor that reads the identification code and the action from the memory device, and that performs the action stored in the memory device in response to reading the identification code.

6. The oximeter system of claim 5 wherein said action comprises said oximeter monitor displaying the sensor model of said oximeter sensor by decoding said identification code.

7. An oximeter system comprising:

an oximeter sensor that includes a light emitting element, a light detecting element, and a memory device that stores digital data, said digital data comprising a code identifying a manufacturer of said oximeter sensor and an action to be performed by an oximeter monitor coupled to the oximeter sensor in response to reading the code, the action stared in the memory device indicating that the oximeter monitor is to use the code to determine whether the sensor is compatible with the oximeter monitor; and an oximeter monitor that reads the code and the action from the memory device, and that performs the action stored in the memory device by using the code to determine whether the sensor is compatible with the oximeter monitor.

8. A method for operating an oximeter system, the method comprising:

emitting light from a light emitting element in an oximeter sensor;

detecting light from the light emitting element using a photodetector in the sensor;

storing digitally encoded data in a memory in the sensor, the digitally encoded data comprising an identification code that identifies a sensor model of said oximeter sensor in said memory and an action that indicates a function to be performed by an oximeter monitor coupled to the oximeter sensor in response to reading the identification code;

reading said identification code and said action from the memory using said oximeter monitor; and performing the function indicated by said action using said oximeter monitor.

9. The method of claim 8 wherein performing the function indicated by said action comprises:

displaying the sensor model of said oximeter sensor by decoding said identification code.

10. A method for operating an oximeter system, the method comprising:

emitting light from a light emitting element in an oximeter sensor;

detecting light from the light emitting element using a photodetector in the sensor;

storing digitally encoded data in a memory in the sensor, the digitally encoded data comprising a code identifying a manufacturer of said oximeter sensor in said memory, and an action that indicates a function to be performed by an oximeter monitor coupled to the oximeter sensor in response to reading said code;

reading said identification code and said action from the memory using said oximeter monitor; and performing the function indicated by said action using said oximeter monitor.

11. The method of claim 10 wherein performing the function indicated by said action comprises:

displaying the manufacturer of said oximeter sensor by decoding said identification code.

* * * * *